United States Patent
Wu et al.

(10) Patent No.: US 12,269,823 B2
(45) Date of Patent: Apr. 8, 2025

(54) CRYSTAL FORM OF PYRIDOPYRIMIDINE DERIVATIVE AND PREPARATION METHOD THEREOF

(71) Applicants: JIANGSU HENGRUI MEDICINE CO., LTD., Jiangsu (CN); SHANGHAI HENGRUI PHARMACEUTICAL CO., LTD., Shanghai (CN)

(72) Inventors: Qi Wu, Jiangsu (CN); Zhenxing Du, Jiangsu (CN); Jie Wang, Jiangsu (CN); Lin Wang, Jiangsu (CN); Weidong Lu, Shanghai (CN); Qiyun Shao, Shanghai (CN); Jun Feng, Shanghai (CN); Feng He, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 485 days.

(21) Appl. No.: 17/757,946

(22) PCT Filed: Dec. 31, 2020

(86) PCT No.: PCT/CN2020/142037
§ 371 (c)(1),
(2) Date: Jun. 24, 2022

(87) PCT Pub. No.: WO2021/136488
PCT Pub. Date: Jul. 8, 2021

(65) Prior Publication Data
US 2023/0058425 A1 Feb. 23, 2023

(30) Foreign Application Priority Data
Jan. 2, 2020 (CN) .......................... 202010002822.9

(51) Int. Cl.
*C07D 471/04* (2006.01)
(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

FOREIGN PATENT DOCUMENTS

| CN | 107108615 A | 8/2017 | |
|---|---|---|---|
| WO | 2012058671 A1 | 5/2012 | |
| WO | WO-2017048727 A1 * | 3/2017 | ........... A61K 31/519 |
| WO | 2018045150 A1 | 3/2018 | |
| WO | 2019166532 A1 | 9/2019 | |
| WO | 2020007275 A1 | 1/2020 | |

OTHER PUBLICATIONS

International Search Report issued Mar. 26, 2021 in PCT/CN2020/142037.

* cited by examiner

*Primary Examiner* — Adam C Milligan
*Assistant Examiner* — Ernesto Valle
(74) *Attorney, Agent, or Firm* — Ice Miller LLP

(57) ABSTRACT

The present disclosure relates to a crystal form of a pyridopyrimidine derivative and a preparation method thereof, and specifically relates to the crystal form of the compound of formula (I) and a preparation method thereof. The new crystal form has good physical and chemical properties, thereby facilitating clinical treatments.

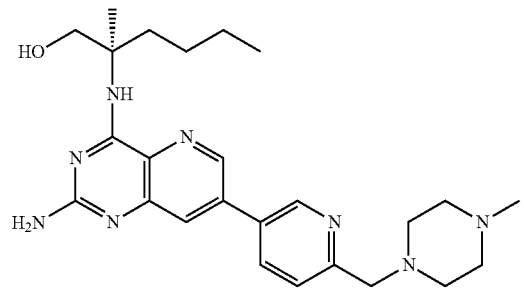

17 Claims, 6 Drawing Sheets

CRYSTAL FORM OF PYRIDOPYRIMIDINE DERIVATIVE AND PREPARATION METHOD THEREOF

CROSS-REFERENCE TO RELATED APPLICATION

This application is a Section 371 of International Application No. PCT/CN2020/142037 filed Dec. 31, 2020, which was published in the Chinese language Jul. 8, 2021, under International Publication No. WO 2021/136488 A1, which claims priority to Chinese Patent Application No. 202010002822.9 filed Jan. 2, 2020, the disclosures of which are incorporated herein by reference in their entireties.

TECHNICAL FIELD

The present disclosure relates to a crystalline form of pyridopyrimidine derivative and a method for preparing the same, and specifically, to a crystalline form of a compound of formula (I) and a method for preparing the same.

BACKGROUND

Toll-like receptors (TLRs) are an important group of receptors involved in innate immunity. TLRs are non-catalytic single-pass membrane receptors that are usually expressed on sentinel cells such as macrophages and dendritic cells and can recognize structurally conserved molecules derived from microbes. Once these microbes have broken through physical barriers such as the skin or intestinal tract mucosa, they are recognized by TLRs, thereby activating immune cell responses (Mahla, R S., et al., *Front Immunol.*, 4:248 (2013)). The ability of the immune system to recognize a broad range of pathogenic microorganisms is due in part to the widespread presence of Toll-like immune receptors.

There are at least 10 different TLRs in mammals. Ligands for some of these receptors and the corresponding signaling cascades have been identified. TLR8 is a member of a subgroup of TLRs (TLRs 3, 7, 8 and 9), and is restricted to the endosomal compartment of cells that specifically recognize heterologous nucleic acids. TLR8 is expressed in humans primarily by monocytes, NK cells and myeloid dendritic cells (mDCs). TLR8 agonists can result in the release of a variety of proinflammatory cytokines, such as IL-6, IL-12, TNF-α and IFN-γ. TLR8 plays an important role in both innate and adaptive immunities in organisms. TLR8 agonists are immune modulators that can be used for the treatment of various immune-related diseases, such as ovarian cancer, melanoma, non-small cell lung cancer, hepatocellular carcinoma, basal cell carcinoma, renal cell carcinoma, myeloma, allergic rhinitis, asthma, chronic obstructive pulmonary disease (COPD), ulcerative colitis, hepatic fibrosis, and viral infections of HBV, *Flaviviridae* virus, HCV, HPV, RSV, SARS, HIV, and influenza.

Since TLR8 and TLR7 are highly homologous, TLR8 agonists are also TLR7 agonists in most cases. Thus dual agonists of TLR8 and TLR7 have been reported in many patents, such as Patent Publication Nos. WO2009111337, WO2011017611, WO2011068233, WO2011139348, WO2012066336, WO2013033345 and WO2017046112. Only a few selective agonists for TLR8, mainly VTX-2337 by VentiRX (WO2007024612) and GS-9688 by Gilead (WO2016141092), have been reported, but the two compounds still have certain activity on TLR7 and also have poor selectivity for Cyp and hERG. Thus a need to develop TLR8 agonists of higher safety and efficacy is still present.

Patent No. WO2020007275 (Application No. PCT/CN/2019/094310) discloses a compound of formula (I), named (R)-2-((2-amino-7-(6-((4-methylpiperazin-1-yl)methyl)pyridin-3-yl)pyrido[3,2-d]pyrimidin-4-yl)amino)-2-methyl-hexan-1-ol, which is a novel TLR8 agonist with improved properties in clinical efficacy or indications, safety, etc., the compound having a structure shown below:

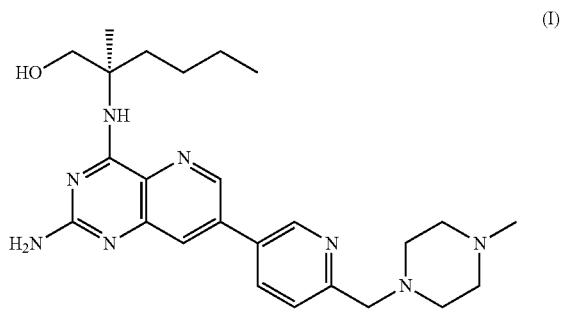 [SMILES: CCCC[C@](C)(CO)Nc1nc(N)nc2cc(-c3ccc(CN4CCN(C)CC4)nc3)cnc12]

(I)

The structure of a crystalline form of a pharmaceutical active ingredient generally affects the chemical stability of a medicine, and the differences in crystallization conditions and storage conditions may cause changes in the structure of the crystalline form of the compound and sometimes generation of other crystalline forms. Generally, amorphous drug products have no regular crystalline form structure and often have other defects, such as poor product stability, fine powder, difficulty in filtration, ease of agglomeration and poor flowability. Therefore, it is necessary to improve various properties of the above products, and intensive research is needed to explore novel crystalline forms with high purity and chemical stability.

SUMMARY

The present disclosure is intended to provide a novel crystalline form of a compound of formula (I), which has good stability and can be better applied to clinical applications.

In one aspect, the present disclosure provides a crystalline form A of the compound of formula (I), having an X-ray powder diffraction pattern with characteristic peaks at 2θ angles of 8.610, 9.740, 13.903, 15.313, 16.354, 17.675, 17.879, 19.184, 19.905, 20.901, 21.365, 22.319 and 23.057,

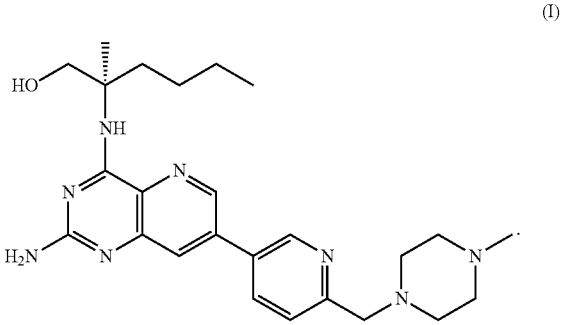 [SMILES: CCCC[C@](C)(CO)Nc1nc(N)nc2cc(-c3ccc(CN4CCN(C)CC4)nc3)cnc12]

(I)

In certain embodiments, the present disclosure provides a crystalline form A of the compound of formula (I), having an X-ray powder diffraction pattern with characteristic peaks at 2θ angles of 8.610, 9.740, 10.949, 13.314, 13.903, 15.313, 16.060, 16.354, 16.794, 17.675, 17.879, 19.184, 19.905, 20.901, 21.365, 22.319, 23.057, 23.748, 24.430, 25.428, 26.576, 27.270, 27.863, 28.957, 29.842 and 31.506.

In certain embodiments, the present disclosure provides a crystalline form A of the compound of formula (I), having an X-ray powder diffraction pattern as shown in FIG. 2.

The present disclosure further provides a method for preparing the crystalline form A of the compound of formula (I) above, comprising:
mixing the compound of formula (I) with a proper amount of a solvent, and evaporating for crystallization, wherein the solvent may be one or more of methanol, n-heptane, cyclohexane, n-hexane, petroleum ether and n-propanol; or,
mixing the compound of formula (I) with a proper amount of a solvent, heating for dissolution, and cooling for crystallization, wherein the solvent may be ethyl acetate.

The disclosure provides a crystalline form B of the compound of formula (I), having an X-ray powder diffraction pattern with characteristic peaks at 2θ angles of 4.60, 8.77, 9.90, 13.86, 15.45, 16.44, 17.74, 18.03, 19.31, 19.91, 21.07, 21.52, 22.48 and 23.22,

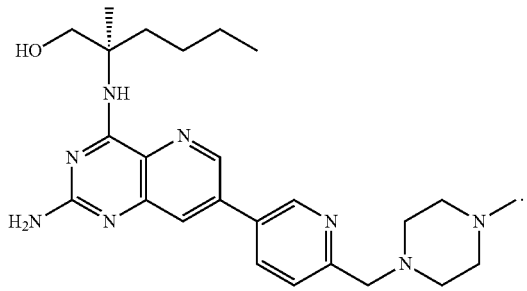

(I)

In certain embodiments, the present disclosure provides a crystalline form B of the compound of formula (I), having an X-ray powder diffraction pattern with characteristic peaks at 2θ angles of 4.60, 8.77, 9.20, 9.90, 11.17, 13.86, 14.51, 15.45, 16.44, 17.74, 18.03, 18.19, 18.51, 19.31, 19.91, 20.07, 21.07, 21.52, 22.48, 23.22, 24.00, 24.61, 25.64, 26.78, 27.43, 28.04, 29.31, 31.21, 32.09, 32.57, 33.23 and 34.01.

In certain embodiments, the present disclosure provides a crystalline form B of the compound of formula (I), having an X-ray powder diffraction pattern as shown in FIG. 4.

The present disclosure further provides a method for preparing the crystalline form B of the compound of formula (I) above, comprising:
mixing the compound of formula (I) with a proper amount of a solvent, and evaporating for crystallization, wherein the solvent may be one or more of water, isopropanol, ethyl acetate, acetonitrile, acetophenone, dichloromethane, N,N-dimethylformamide and 1,2-dichloroethane; or,
mixing the compound of formula (I) with a proper amount of a solvent, heating for dissolution, and cooling for crystallization, wherein the solvent may be isopropanol or dimethyl sulfoxide.

The crystalline form obtained by the present disclosure is subjected to structure determination and crystalline form studies through X-ray powder diffraction pattern (XRPD) and differential scanning calorimetry (DSC).

In certain embodiments, a mixture of the crystalline form A and the crystalline form B can be prepared by using certain solvents, for example, by mixing the compound of formula (I) with a proper amount of a solvent (such as acetone, isopropyl acetate, methyl t-butyl ether, 2-butanone, methyl isobutyl ketone, nitromethane, ethyl acetate/n-heptane, butyl acetate, p-xylene, propylene glycol monomethyl ether, isopentanol, water/ethanol, water/acetone, ethyl acetate/ethanol and trichloromethane) and evaporating for crystallization. The X-ray powder diffraction pattern is shown in FIG. 6.

The crystallization methods for the crystalline form in the present disclosure are conventional, such as crystallization by evaporating, crystallization by cooling or room-temperature crystallization.

The starting materials used in the method for preparing the crystalline form disclosed herein may be any form of the compound of formula (I), including but not limited to: an amorphous form, any crystalline form, a hydrate, a solvate and the like.

The present disclosure further provides a pharmaceutical composition comprising: the crystalline form A and/or the crystalline form B of the compound of formula (I) above, and one or more pharmaceutically acceptable carriers or excipients.

The present disclosure further provides a pharmaceutical composition prepared by mixing the crystalline form A and/or the crystalline form B of the compound of formula (I) above with one or more pharmaceutically acceptable carriers or excipients.

The present disclosure further provides a method for preparing a pharmaceutical composition, comprising: mixing the crystalline form A and/or the crystalline form B of the compound of formula (I) above with one or more pharmaceutically acceptable carriers or excipients.

The present disclosure further provides use of the crystalline form A or the crystalline form B of the compound of formula (I) or the pharmaceutical composition disclosed herein in preparing a medicament for agonizing TLR8.

The present disclosure further provides use of the crystalline form A or the crystalline form B of the compound of formula (I) or the pharmaceutical composition disclosed herein in preparing a medicament for treating an infection caused by a virus, wherein the virus is preferably one or more of hepatitis B virus, hepatitis C virus, influenza virus, herpes virus and human immunodeficiency virus.

The present disclosure further provides use of the crystalline form A or the crystalline form B of the compound of formula (I) or the pharmaceutical composition disclosed herein in preparing a medicament for modulating immune system.

The present disclosure further provides use of the crystalline form A or the crystalline form B of the compound of formula (I) or the pharmaceutical composition disclosed herein in preparing a medicament for treating or preventing a tumor.

In the specification and claims of the present application, unless otherwise specified, the scientific and technological terms used herein have meanings generally understood by those skilled in the art. However, definitions and explanations for some of the related terms are provided below for a better understanding of the present disclosure. In addition, if the definitions and explanations of the terms provided herein are not consistent with the meanings generally understood by those skilled in the art, the definitions and explanations of the terms provided herein shall prevail.

The "slurrying" described herein refers to a purification method by utilizing the low solubility of the target substance and high solubility of the impurities in a solvent, which is capable of decoloring, changing the crystalline form or removing small amounts of impurities.

The "X-ray powder diffraction pattern" or "XRPD" described herein refers to a set of X-ray powder diffraction peaks obtained according to the Bragg's equation 2d sin θ=nλ (in the formula, λ is the wavelength of X-ray, the diffraction order n is any positive integer, and the first-order diffraction peak is generally taken, i.e., n=1). When X-ray is incident on a certain atomic plane with the d-lattice plane spacing of a crystal or a partial crystal sample at a grazing angle θ (the complementary angle of incidence, also known as Bragg angle), the Bragg's equation can be satisfied.

The "X-ray powder diffraction pattern" or "XRPD" described herein refers to a pattern obtained by using Cu—Kα radiation in an X-ray powder diffractometer.

The "differential scanning calorimetry" or "DSC" described herein refers to measurement of the temperature difference and heat flow difference between a sample and a reference substance during a ramping or thermostatic process to characterize all the physical changes and chemical changes related to the thermal effect, and to obtain the phase change information of the sample.

The "2θ" or "angle 2θ" described herein refers to diffraction angle. θ is the Bragg angle in unit ° or degree. The margin of error for 2θ may be ±0.3, ±0.2 or ±0.1.

The "interplanar spacing (d)" described herein refers to 3 selected non-parallel unit vectors (a, b and c), each of which connects two adjacent lattice points and all of which divide the lattice into juxtaposed parallelepiped units. The lattice is divided according to the determined parallelepiped unit connecting lines, giving a set of linear grids called space lattice or crystal lattice. The lattice and the crystal lattice reflect the periodicity of the crystal structure by using geometrical points and lines, respectively. The interplanar distances (the distance between two adjacent parallel crystal planes) for different crystal planes are different; the unit is Å.

Beneficial Effects

The crystalline form A and crystalline form B of the compound of formula (I) prepared by the present disclosure feature high purity, high crystalline form stability under the conditions of illumination, high temperature and high humidity, minor changes HPLC purity and high physical and chemical stabilities, and are more favorable for storage and use as raw materials.

DETAILED DESCRIPTION

Figure 1:
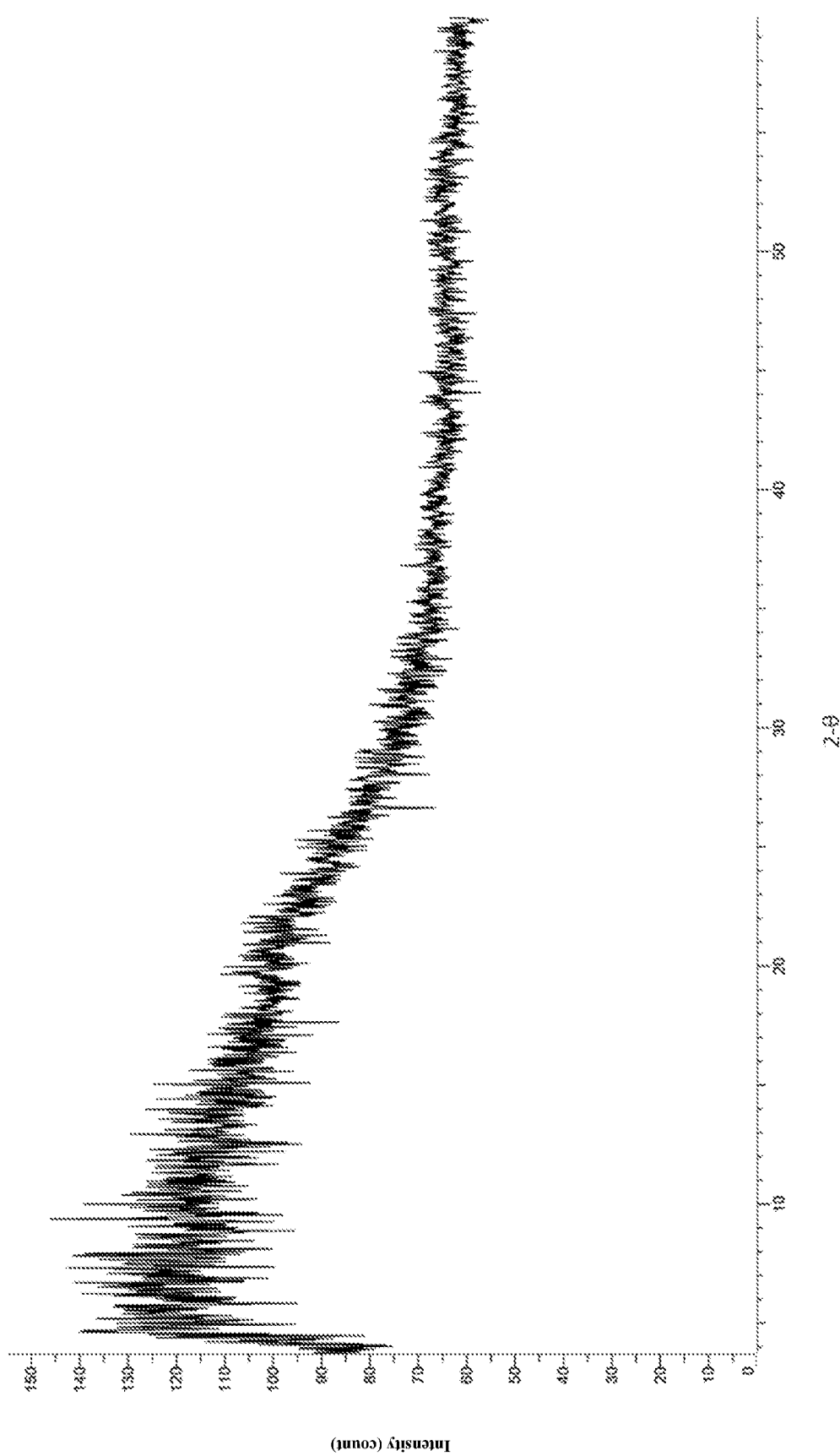
FIG. 1 is an XRPD pattern for an amorphous form of the compound of formula (I).

Hereinafter, the present disclosure will be explained in more details with reference to the examples. The examples are only used to illustrate the technical solutions of the present disclosure, rather than limit the essence and scope of the present disclosure.

Test conditions of the instruments used in the test:
1. Differential scanning calorimeter (DSC)
Model: Mettler Toledo DSC 1 STAR$^e$ System.
Purging gas: nitrogen.
Ramping rate: 10.0° C./min.
Temperature range: 40-300° C.
2. Differential scanning calorimeter (DSC)
Model: Mettler Toledo DSC 3+.
Purging gas: nitrogen.
Ramping rate: 10.0° C./min.
Temperature range: 25-300° C.
3. X-ray powder diffractometer (XRPD)
Model: BRUKER D8 DISCOVERY X-ray powder diffractometer.
X-ray: monochromatic Cu—Kα ray (Cu—Kα1 wavelength is 1.5406 Å, Cu—Kα2 wavelength is 1.54439 Å, and Cu—Kα wavelength takes a weighted average of Kα1 and Kα2λ=1.5418 Å).
Scanning mode: θ/2θ scanning range: 5-48°.
Voltage: 40 kV, current: 40 mA.
4. X-ray powder diffractometer (XRPD)
Model: BRUKER D8 Focus X-ray powder diffractometer.
X-ray: monochromatic Cu—Kα ray (Cu—Kα1 wavelength is 1.5406 Å, Cu—Kα2 wavelength is 1.54439 Å, and Cu—Kα wavelength takes a weighted average of Kα1 and Kα2λ=1.5418 Å).
Scanning mode: θ/2θ scanning range: 2-40°.
Voltage: 40 kV, current: 40 mA.
The angel 2θ was measured by BRUKER D8 Focus X-ray powder diffractometer, rounded to 2 decimal digits.

In the examples, the reactions were performed in an argon atmosphere or a nitrogen atmosphere unless otherwise specified.

An argon atmosphere or a nitrogen atmosphere means that the reaction flask is connected to a balloon containing about 1 L of argon or nitrogen.

A hydrogen atmosphere means that the reaction flask is connected to a balloon containing about 1 L of hydrogen.

Parr 3916EKX hydrogenator, Qinglan QL-500 hydrogenator or HC2-SS hydrogenator was used for pressurized hydrogenation reactions.

The hydrogenation reaction usually involved 3 cycles of vacuumization and hydrogen purge.

A CEM Discover-S 908860 microwave reactor was used for the microwave reaction.

In the examples, a solution refers to an aqueous solution unless otherwise specified.

In the examples, the reaction temperature was room temperature, i.e., 20° C. to 30° C., unless otherwise specified.

The monitoring of the reaction progress in the examples was conducted by thin layer chromatography (TLC). The developing solvent for reactions, the eluent system for column chromatography purification and the developing solvent system for thin layer chromatography included: A: dichloromethane/methanol system, B: n-hexane/ethyl acetate system, and C: petroleum ether/ethyl acetate system. The volume ratio of the solvents was adjusted according to the polarity of the compound, or by adding a small amount of basic or acidic reagents such as triethylamine and acetic acid.

Example 1

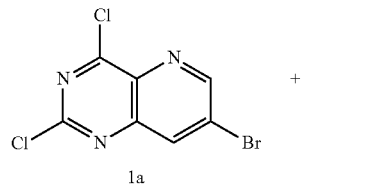
1a

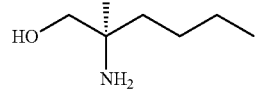
1b

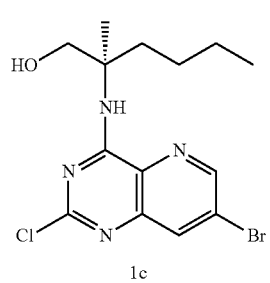
1c

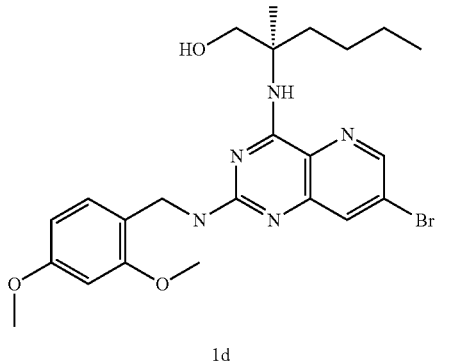
1d

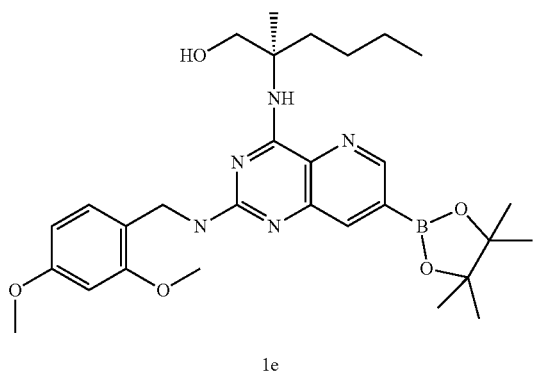
1e

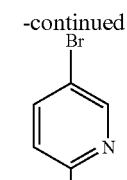
1f

1g

I

Step 1

(R)-2-((7-bromo-2-chloropyrido[3,2-d]pyrimidin-4-yl)amino)-2-methylhexan-1-ol 1c Compound 1a (400 mg, 1.434 mmol, prepared using the method disclosed in patent Application No. WO2014022728) was added to 10 mL of tetrahydrofuran before (R)-2-amino-2-methylhexan-1-ol 1b (377 mg, 2.873 mmol) and N,N-diisopropylethylamine (556 mg, 4.302 mmol) were added. The reaction system was stirred at 100° C. for 16 h in a sealed tube. Upon completion of the reaction, the reaction mixture was cooled to room temperature and filtered to remove the insoluble substances. The filtrate was concentrated at reduced pressure, and the resulting residue was purified by silica gel column chromatography with the eluent system A to give the target product 1c (4.0 g, 55.3% yield).

MS m/z (ESI): 373.1 [M+1].

Step 2

(R)-2-((7-bromo-2-((2,4-dimethoxybenzyl)amino)pyrido[3,2-d]pyrimidin-4-yl)amino)-2-methylhexan-1-ol 1d Compound 1c (250 mg, 0.669 mmol) was added to 10 mL of tetrahydrofuran before 2,4-dimethoxybenzylamine (560 mg, 3.349 mmol) and N,N-diisopropylethylamine (259 mg, 2.004 mmol) were added. The reaction system was stirred at 100° C. for 16 h in a sealed tube. 20 mL of water was added to the reaction mixture, and dichloromethane (20 mL×3) was added for extraction. The organic phases were combined, washed with water (20 mL) and saturated sodium chloride solution (20 mL), dried over anhydrous magnesium sulfate and filtered to remove the desiccant. The filtrate was concentrated at reduced pressure, and the resulting residue was purified by silica gel column chromatography with the eluent system B to give the target product 1d (295 mg, 87.5% yield).

MS m/z (ESI): 504.1 [M+1]

Step 3

(R)-2-((2-((2,4-dimethoxybenzyl)amino)-7-(4,4,5,5-tetramethyl-1,3,2-dioxaborolan-2-yl)pyrido[3,2-d]pyrimidin-4-yl)amino)-2-methylhexan-1-ol 1e Compound 1d (295 mg, 0.54 mmol) was added to 5 mL of ethylene glycol dimethyl ether before bis(pinacolato) diboron (223 mg, 878.169 μmol), [1,1'-bis(diphenylphosphino)ferrocene]palladium(II) dichloride (43 mg, 0.059 mmol) and potassium acetate (173 mg, 1.76 mmol) were sequentially added. The system was purged with argon three times, heated to 80° C. and stirred for 2 h. The reaction mixture was concentrated at reduced pressure. 20 mL of water was added to the mixture before dichloromethane (10 mL×3) was added for extraction. The organic phases were combined, washed with water (20 mL) and saturated sodium chloride solution (20 mL), dried over anhydrous magnesium sulfate and filtered to remove the desiccant. The filtrate was concentrated at reduced pressure to give the crude target product 1e (322 mg, 100% yield).

Step 4

(R)-2-((2-((2,4-dimethoxybenzyl)amino)-7-(6-((4-methylpiperazin-1-yl)methyl)pyridin-3-yl)pyrido[3,2-d]pyrimidin-4-yl)amino)-2methylhexan1-ol 1g Compound 1e (650 mg, 1.178 mmol) was added to a mixture of 20 mL of 1,4-dioxane and 4 mL of water before 1-((5-bromopyridin-2-yl)methyl)-4-methylpiperazine 1f (318 mg, 1.170 mmol, prepared by the method disclosed in Patent Application No. WO20020026052), [1,1'-bis(diphenylphosphino)ferrocene]palladium(II) dichloride (86 mg, 0.117 mmol) and potassium carbonate (489 mg, 3.538 mmol) were added. The system was purged with argon three times, heated to 80° C. and stirred for 2 h. The reaction mixture was concentrated at reduced pressure. 30 mL of water was added before dichloromethane (30 mL×3) was added for extraction. The organic phases were combined, washed with water (30 mL) and saturated sodium chloride solution (30 mL), dried over anhydrous magnesium sulfate and filtered to remove the desiccant. The filtrate was concentrated at reduced pressure, and the resulting residue was purified by silica gel column chromatography with the eluent system B to give the target product 1g (650 mg, 89.70% yield).

MS m/z (ESI): 615.1 [M+1].

Step 5

(R)-2-((2-amino-7-(6-((4-methylpiperazin-1-yl)methyl)pyridin-3-yl)pyrido[3,2-d]pyrimidin-4-yl)amino)-2-methylhexan-1-ol I Compound 1g (650 mg, 0.138 mmol) was added to 5 mL of trifluoroacetic acid. The system was reacted at room temperature for 3 h, and the reaction mixture was concentrated at reduced pressure. 20 mL of saturated sodium bicarbonate was added to the concentrated reaction mixture before dichloromethane (20 mL×3) was added for extraction. The organic phases were combined, washed with saturated sodium chloride solution (30 mL), dried over anhydrous magnesium sulfate and filtered to remove the desiccant. The filtrate was concentrated at reduced pressure, and the resulting residue was purified by silica gel column chromatography with the eluent system B to give product I (320 mg, 65.14% yield). X-ray powder diffraction determined that the compound is an amorphous form, and the XRPD pattern was shown in FIG. 1.

MS m/z (ESI): 465.1 [M+1]

$^1$H NMR (400 MHz, DMSO-$d_6$) δ 8.87-8.88 (d, 1H), 8.60-8.61 (m, 1H), 8.14-8.16 (d, 1H), 7.79-7.80 (s, 1H), 7.51-7.53 (d, 1H), 7.20 (s, 1H), 6.36 (br, 2H), 5.12-5.15 (t, 1H), 3.66 (s, 2H), 3.68-3.70 (m, 1H), 3.48-2.53 (m, 1H), 2.32-3.42 (m, 8H), 2.12 (s, 3H), 1.90-1.92 (m, 2H), 1.40 (s, 3H), 1.22-1.23 (m, 4H), 0.80-0.84 (m, 3H).

Example 2

The compound of formula (I) obtained in Example 1 (200 mg, 0.43 mmol) was added to 10 mL of ethyl acetate. The mixture was heated at reflux, stirred for dissolving, slowly cooled to room temperature, stirred and filtered. The filter cake was washed with ethyl acetate, collected and dried in vacuo to give 100 mg of crystalline form A of the compound of formula (I) with characteristic peak positions as shown in the following table:

TABLE 1

XRD characteristic peak positions for crystalline form A

| Peak number | 2θ [°] | d [Å] | I [%] |
|---|---|---|---|
| Peak 1 | 8.610 | 10.26190 | 10.4 |
| Peak 2 | 9.740 | 9.07396 | 12.2 |
| Peak 3 | 10.949 | 8.07412 | 6.7 |
| Peak 4 | 13.314 | 6.64495 | 26.4 |
| Peak 5 | 13.903 | 6.36460 | 18.2 |
| Peak 6 | 15.313 | 5.78147 | 77.2 |
| Peak 7 | 16.060 | 5.51419 | 28.1 |
| Peak 8 | 16.354 | 5.41587 | 58.8 |
| Peak 9 | 16.794 | 5.27492 | 24.5 |
| Peak 10 | 17.675 | 5.01392 | 83.2 |
| Peak 11 | 17.879 | 4.95721 | 100.0 |
| Peak 12 | 19.184 | 4.62284 | 33.6 |
| Peak 13 | 19.905 | 4.45695 | 27.8 |
| Peak 14 | 20.901 | 4.24682 | 25.8 |
| Peak 15 | 21.365 | 4.15559 | 67.5 |
| Peak 16 | 22.319 | 3.98004 | 50.2 |
| Peak 17 | 23.057 | 3.85426 | 42.3 |
| Peak 18 | 23.748 | 3.74370 | 13.4 |
| Peak 19 | 24.430 | 3.64063 | 31.5 |
| Peak 20 | 25.428 | 3.49996 | 47.0 |
| Peak 21 | 26.576 | 3.35135 | 22.2 |
| Peak 22 | 27.270 | 3.26761 | 26.7 |
| Peak 23 | 27.863 | 3.19940 | 25.9 |
| Peak 24 | 28.957 | 3.08098 | 4.6 |
| Peak 25 | 29.842 | 2.99166 | 1.5 |
| Peak 26 | 31.506 | 2.83726 | 13.6 |
| Peak 27 | 32.420 | 2.75938 | 12.9 |

Example 3

The compound of formula (I) (400 mg, 0.86 mmol) was added into 8 mL of isopropanol. The mixture was heated at reflux until solid was dissolved, naturally cooled to room temperature, stirred and filtered. The filter cake was washed with isopropanol, collected and dried in vacuo to give 200 mg of crystalline form B of the compound of formula (I) with characteristic peak positions as shown in the following table:

TABLE 2

XRD characteristic peak positions for crystalline form B

| Peak number | 2θ [°] | d [Å] | I [%] |
| --- | --- | --- | --- |
| Peak 1 | 4.60 | 19.186 | 100 |
| Peak 2 | 8.77 | 10.075 | 0.1 |
| Peak 3 | 9.20 | 9.605 | 0.3 |
| Peak 4 | 9.90 | 8.925 | 0.2 |
| Peak 5 | 11.17 | 7.914 | 0.1 |
| Peak 6 | 13.86 | 6.386 | 0.2 |
| Peak 7 | 14.51 | 6.099 | 0.1 |
| Peak 8 | 15.45 | 5.730 | 0.1 |
| Peak 9 | 16.44 | 5.386 | 0.3 |
| Peak 10 | 17.74 | 4.996 | 0.7 |
| Peak 11 | 18.03 | 4.916 | 0.3 |
| Peak 12 | 18.19 | 4.873 | 0.4 |
| Peak 13 | 18.51 | 4.789 | 1.8 |
| Peak 14 | 19.31 | 4.593 | 0.2 |
| Peak 15 | 19.91 | 4.456 | 0.2 |
| Peak 16 | 20.07 | 4.422 | 0.1 |
| Peak 17 | 21.07 | 4.214 | 0.2 |
| Peak 18 | 21.52 | 4.126 | 0.3 |
| Peak 19 | 22.48 | 3.953 | 0.6 |
| Peak 20 | 23.22 | 3.828 | 0.7 |
| Peak 21 | 24.00 | 3.705 | 0.2 |
| Peak 22 | 24.61 | 3.614 | 0.1 |
| Peak 23 | 25.64 | 3.472 | 0.2 |
| Peak 24 | 26.78 | 3.326 | 0.1 |
| Peak 25 | 27.43 | 3.248 | 0.4 |
| Peak 26 | 28.04 | 3.180 | 0.2 |
| Peak 27 | 29.31 | 3.045 | 0.1 |
| Peak 28 | 31.21 | 2.863 | 0.1 |
| Peak 29 | 32.09 | 2.787 | 0.1 |
| Peak 30 | 32.57 | 2.747 | 0.1 |
| Peak 31 | 33.23 | 2.694 | 0.1 |
| Peak 32 | 34.01 | 2.634 | 0.1 |

Example 4

The crystalline form A and crystalline form B of the compound of formula (I) were transferred and let stand in clean open weighing bottles to test the stability under the conditions of heating (40° C., 60° C.), illumination (4500 1×±500 1×) and high humidity (90%±5%, 75%±5%) during an inspection period of 30 days.

TABLE 3

Result of a 30-day influencing factor test for crystalline form A

| Conditions | Time (days) | Purity (%) | Crystalline form |
| --- | --- | --- | --- |
| Initial | 0 | 97.83 | A |
| 4500 lux | 5 | 95.82 | |
| | 10 | 94.99 | |
| | 30 | 92.51 | A |
| 40° C. | 5 | 96.98 | |
| | 10 | 96.98 | |
| | 30 | 95.47 | A |
| 60° C. | 5 | 95.87 | |
| | 10 | 95.72 | |
| | 30 | 93.74 | A |
| RH 75% | 5 | 97.83 | |
| | 10 | 97.85 | |
| | 30 | 97.47 | A |
| RH 90% | 5 | 97.91 | |
| | 10 | 97.84 | |
| | 30 | 97.53 | A |

TABLE 4

Result of a 30-day influencing factor test for crystalline form B

| Conditions | Time (days) | Purity (%) | Crystalline form |
| --- | --- | --- | --- |
| Initial | 0 | 98.65 | B |
| 4500 lux | 5 | 95.48 | |
| | 10 | 92.61 | |
| | 30 | 88.03 | B |
| 40° C. | 5 | 98.19 | |
| | 10 | 98.17 | |
| | 30 | 97.23 | B |
| 60° C. | 5 | 97.87 | |
| | 10 | 97.53 | |
| | 30 | 96.24 | B |
| RH 75% | 5 | 98.65 | |
| | 10 | 98.69 | |
| | 30 | 97.96 | B |
| RH 90% | 5 | 98.69 | |
| | 10 | 98.75 | |
| | 30 | 97.99 | B |

Example 5

The crystalline form B of the compound of formula (I) was examined for the stability under long-term (25° C., 60% RH) and accelerated (40° C., 75% RH) conditions in a period of 3 months. The results are shown in the following table:

TABLE 5

Stabilities of crystalline form B of compound of formula (I) under long-term and accelerated conditions

| Sample | Condition of standing | Purity (%) | | | | Crystalline form |
|---|---|---|---|---|---|---|
| | | Initial | Month 1 | Month 2 | Month 3 | |
| Crystalline form B | 25° C., 60% RH | 99.71 | 99.70 | 99.71 | 99.62 | B |
| | 40° C., 75% RH | 99.71 | 99.69 | 99.68 | 99.54 | B |

The experimental results show that: the crystalline form B of the compound of formula (I) has good physical and chemical stabilities when placed for 3 months under long-term (25° C., 60% RH) and accelerated (40° C., 75% RH) conditions.

TEST EXAMPLES

Biological Evaluation

Test example 1. Determination of agonist activity of the compound disclosed herein on human TLR8 and TLR7

The hTLR8-activating effect of the compound disclosed herein on the expression in HEK-blue™ hTLR8 stably transfected cells was determined by the following procedures:

I. Materials and Instruments
  1. DMEM (Gibco, 10564-029),
  2. Fetal bovine serum (GIBCO, 10099),
  3. Trypan blue solution (Sigma, T8154-100ML),
  4. Flexstation 3 Multi-Mode Microplate Reader (Molecular Devices),
  5. HEK-blue™ hTLR8 cells (InvivoGen, hkb-hTLR8), or HEK-blue™ hTLR7 cells (InvivoGen, hkb-hTLR7),
  6. HEK-Blue detection reagent (InvivoGen, hb-det3),
  7. Phosphate buffered saline (PBS) pH7.4 (Shanghai BasalMedia Technologies Co., LTD., B320).

II. Procedures
  a. Determination of agonist activity on human TLR8
  HEK-Blue detection culture medium was prepared by dissolving HEK-Blue detection agent in 50 mL of endotoxin-free water. The solution was incubated in an incubator at 37° C. for 10 min before sterile filtration. The compound was prepared into a 20 mM stock solution. The stock solution was diluted with pure DMSO to a maximum concentration of $6 \times 10^6$ nM, and then serially 3-fold diluted to the $10^{th}$ concentration. The solutions were 20-fold diluted with culture medium, and added to the wells at a volume of 20 μL.
  HEK-blue™ hTLR8 cells were taken and the supernatant was discarded. 2-5 mL of pre-warmed PBS was added. The cells were incubated in an incubator for 1-2 minutes, gently mixed, stained with trypan blue and counted. The cells were resuspended using HEK-Blue detection culture medium, and adjusted to a cell density of $2.2 \times 10^5$ cells/mL. 180 μL of the cell suspension was added into the 96-well cell culture plate containing 20 μL of the compound. The cells were incubated at 37° C. for 6-16 h.
  The plate was detected using a microplate reader at a wavelength of 620 nm. Corresponding OD value was thus obtained, and the $EC_{50}$ value of the compound was calculated using Graphpad Prism software.
  b. Determination of agonist activity on human TLR7
  HEK-Blue detection culture medium was prepared by dissolving HEK-Blue detection agent in 50 mL of endotoxin-free water. The solution was incubated in an incubator at 37° C. for 10 min before sterile filtration. The compound was prepared into a 20 mM stock solution. The stock solution was diluted with pure DMSO to a maximum concentration of $6 \times 10^6$ nM, and then serially 3-fold diluted to the $10^{th}$ concentration.
  The prepared solutions were 20-fold diluted with the culture medium, and added to the wells at a volume of 20 μL.
  HEK-blue™ hTLR7 cells were taken and the supernatant was discarded. 2-5 mL of pre-warmed PBS was added. The cells were incubated in an incubator for 1-2 minutes, gently mixed, stained with trypan blue and counted. The cells were resuspended using HEK-Blue detection culture medium, and adjusted to a cell density of $2.2 \times 10^5$ cells/mL. 180 μL of the cell suspension was added into the 96-well cell culture plate containing 20 μL of the compound. The cells were incubated at 37° C. for 6-16 h.
  The plate was detected using a microplate reader at a wavelength of 620 nm. Corresponding OD value was thus obtained, and the $EC_{50}$ value of the compound was calculated using Graphpad Prism software.
  The activating effect of the compound disclosed herein on human TLR8 and TLR7 can be determined by the above test, and the $EC_{50}$ values obtained are shown in Table 1-1.

TABLE 1-1

$EC_{50}$ of the compound disclosed herein for human TLR8 and TLR7

| Example | TLR8 | | TLR7 | |
|---|---|---|---|---|
| | $EC_{50}$ (μM) | Emax (%) | $EC_{50}$ (μM) | Emax (%) |
| 1 | 0.10 | 107 | >30 | 14 |

Conclusion: the compound disclosed herein has a good activating effect on human TLR8 and no activating effect on human TLR7, suggesting that the compound disclosed herein has selectivity for TLR8.

Test example 2. Inhibitory effect of the compound disclosed herein on enzymatic activity of midazolam metabolic site on human liver microsome CYP3A4

The inhibitory effect of the compound disclosed herein on enzymatic activity of midazolam metabolic site on human liver microsome CYP3A4 was determined by the following procedures:

I. Materials and Instruments
  1. Phosphate buffered saline (PBS),
  2. NADPH (Sigma N-1630),
  3. Human liver microsome (Corning Gentest),
  4. ABI QTrap 4000 LC-MS/MS System (AB Sciex),
  5. Inertsil C8-3 column, 4.6×50 mm, 5 μm (Dikma, USA), 6. CYP probe substrate (15 μM midazolam, SIGMA UC429) and positive control inhibitor (ketoconazole, SIGMA K1003).

II. Procedures

A 100 mM PBS buffer was prepared and was used to prepare a 2.5 mg/mL microsome solution and a 5 mM NADPH solution. A compound working solution at 5× concentration was serially diluted with PBS (150, 50, 15, 5, 1.5, 0.15, 0.015 and 0 μM). A ketoconazole working solution at 5× concentration was serially diluted with PBS (150, 50, 15, 5, 1.5, 0.15, 0.015 and 0 μM). A midazolam working solution was diluted to 15 μM with PBS.

The 2.5 mg/mL microsome solution, the 15 μM midazolam working solution, a MgCl$_2$ solution and the compound working solution (150, 50, 15, 5, 1.5, 0.15, 0.015 and 0 μM, with different reaction systems for each concentration), each of 20 μL, were taken and well mixed. For the positive control group, the compound was replaced with ketoconazole at the same concentration. A 5 mM NADPH solution were simultaneously pre-incubated for 5 min at 37° C. After 5 min, 20 μL of NADPH was added to each well to start the reaction and the system was incubated for 30 min. All incubated samples were in duplicate. After 30 minutes, 250 μL of acetonitrile containing internal standard was added to the samples. The samples were mixed well, shaken at 800 rpm for 10 min, and then centrifuged at 3700 rpm for 10 min. 80 μL of the supernatant was taken and subjected to LC-MS/MS analysis.

The IC$_{50}$ values of the drug for the midazolam metabolic site on CYP3A4 were calculated by Graphpad Prism and are shown in Table 1-2.

TABLE 1-2

| IC$_{50}$ values of the compound disclosed herein for midazolam metabolic site on CYP3A4 | |
|---|---|
| Example | IC$_{50}$ (μM) |
| 1 | >30 |

Conclusion: the compound disclosed herein has no inhibitory effect on the midazolam metabolic site on human liver microsome CYP3A4, demonstrating superior safety, suggesting the absence of metabolic drug-drug interaction based on the midazolam metabolic site on CYP3A4.

Test example 3. Inhibitory effect of the compound disclosed herein on enzymatic activity of human liver microsome CYP2D6

The inhibitory effect of the compound disclosed herein on the enzymatic activity of human liver microsome CYP2D6 was determined by the following procedures:

I. Materials and Instruments
1. Phosphate buffered saline (PBS),
2. NADPH (Sigma N-1630),
3. Human liver microsome (Corning Gentest),
4. ABI QTrap 4000 LC-MS/MS System (AB Sciex),
5. Inertsil C8-3 column, 4.6×50 mm, 5 (Dikma, USA),
6. CYP probe substrate (20 μM dextromethorphan, SIGMA Q0750) and positive control inhibitor (quinidine, SIGMA D9684).

II. Procedures

A 100 mM PBS buffer was prepared and was used to prepare a 2.5 mg/mL microsome solution and a 5 mM NADPH solution. A compound working solution at 5× concentration was serially diluted with PBS (150, 50, 15, 5, 1.5, 0.15, 0.015 and 0 μM). A quinidine working solution at 5× concentration was serially diluted with PBS (150, 50, 15, 5, 1.5, 0.15, 0.015 and 0 μM). A dextromethorphan working solution was diluted to 20 μM with PBS.

The 2.5 mg/mL microsome solution, the 20 μM dextromethorphan working solution, a MgCl$_2$ solution and the compound working solution (150, 50, 15, 5, 1.5, 0.15, 0.015 and 0 μM, with different reaction systems for each concentration), each of 20 μL, were taken and well mixed. For the positive control group, the compound was replaced with quinidine at the same concentration. A 5 mM NADPH solution were simultaneously pre-incubated for 5 min at 37° C. After 5 min, 20 μL of NADPH was added to each well to start the reaction and the system was incubated for 30 min. All incubated samples were in duplicate. After 30 minutes, 250 μL of acetonitrile containing internal standard was added to the samples. The samples were mixed well, shaken at 800 rpm for 10 min, and then centrifuged at 3700 rpm for 10 min. 80 μL of the supernatant was taken and subjected to LC-MS/MS analysis.

The IC$_{50}$ values of the drug for metabolic site on CYP2D6 were calculated by Graphpad Prism and are shown in Table 1-3.

TABLE 1-3

| IC$_{50}$ values of the compound disclosed herein for metabolic site on CYP2D6 | |
|---|---|
| Example | IC$_{50}$ (μM) |
| 1 | >30 |

Conclusion: the compound disclosed herein has a weak inhibitory effect on the metabolic activity of human liver microsome CYP2D6, demonstrating superior safety, suggesting the absence of metabolic drug-drug interaction based on CYP2D6.

Test example 4. Inhibitory effect of the compound disclosed herein on enzymatic activity of testosterone metabolic site on human liver microsome CYP3A4

The inhibitory effect of the compound disclosed herein on the enzymatic activity of the testosterone metabolic site on human liver microsome CYP3A4 was determined by the following procedures:

I. Materials and Instruments
1. Phosphate buffered saline (PBS),
2. NADPH (Sigma N-1630),
3. Human liver microsome (Corning Gentest),
4. ABI QTrap 4000 LC-MS/MS System (AB Sciex),
5. Inertsil C8-3 column, 4.6×50 mm, 5 (Dikma, USA),
6. CYP probe substrate (testosterone/100 μM, SIGMA K1003) and positive control inhibitor (ketoconazole, Dr. Ehrenstorfer GmbH, C17322500).

II. Procedures

A 100 mM PBS buffer was prepared and was used to prepare a 2.5 mg/mL microsome solution and a 5 mM NADPH solution. A compound working solution at 5× concentration was serially diluted with PBS (150, 50, 15, 5, 1.5, 0.15, 0.015 and 0 μM). A ketoconazole working solution at 5× concentration was serially diluted with PBS (150, 50, 15, 5, 1.5, 0.15, 0.015 and 0 μM). A dextromethorphan working solution was diluted to 50 μM with PBS.

The 2.5 mg/mL microsome solution, the 50 μM testosterone working solution, a MgCl$_2$ solution and the compound working solution (150, 50, 15, 5, 1.5, 0.15, 0.015 and 0 μM, with different reaction systems for each concentration), each of 20 μL, were taken and well mixed. For the positive control group, the compound was replaced with ketoconazole at the same concentration. A 5 mM NADPH solution were simultaneously pre-incubated for 5 min at 37° C. After 5 min, 20 μL of NADPH was added to each well to start the reaction and the system was incubated for 30 min. All incubated samples were in duplicate. After 30 minutes, 250 μL of acetonitrile containing internal standard was added to the samples. The samples were mixed well, shaken at 800 rpm for 10 min, and then centrifuged at 3700 rpm for 10 min. 80 μL of the supernatant was taken and subjected to LC-MS/MS analysis.

The $IC_{50}$ values of the drug for testosterone metabolic site on CYP3A4 were calculated by Graphpad Prism and are shown in Table 1-4.

TABLE 1-4

| $IC_{50}$ values of the compound disclosed herein for testosterone metabolic site on CYP3A4 | |
| --- | --- |
| Example | $IC_{50}$ (μM) |
| 1 | >30 |

Conclusion: the compound disclosed herein has no inhibitory effect on the testosterone metabolic site on human liver microsome CYP3A4, demonstrating superior safety, suggesting the absence of metabolic drug-drug interaction based on the testosterone metabolic site on CYP3A4.

Test example 5. Determination of the ability of the compound disclosed herein to stimulate IL-12 and IFNγ secretion in peripheral blood mononuclear cells (PBMCs) The ability of the compound disclosed herein to stimulate IL-12 and IFNγ secretion in PBMCs was determined by the following procedures:

I. Materials and Instruments
  1. RPMI 1640 (Invitrogen, 11875),
  2. FBS (Gibco, 10099-141),
  3. Ficoll-Paque PREMIUM (GE, 17-5442-02),
  4. Trypan blue solution (Sigma, T8154-100ML),
  5. SepMateTM-50 (Stemcell, 15460),
  6. Bright-Line™ cytometer (Sigma, Z359629-1EA),
  7. 96-well flat bottom plate (Corning, 3599),
  8. 96-well v-bottom plate (Corning, 3894),
  9. Human IL-12 ELISA kit (NEOBIOSCIENCE, EHC152.96),
  10. Human IFN γ kit (Cisbio, 62HIFNGPEG),
  11. PHERAStar Multi-Mode Microplate Reader (BMG, PHERAStar).

II. Procedures

The compound was diluted with pure DMSO to a maximum concentration of 5 mM, and was then serially 4-fold diluted to the $9^{th}$ concentration. 4 μL of the compound solution was taken and added into 196 μL of RMPI 1640 culture medium containing 10% FBS, and the mixture was well mixed. 50 μL of the mixture was taken and transferred to a new 96-well cell culture plate.

All reagents were equilibrated to room temperature. 60 mL of blood and an equal volume of PBS +2% FBS were added to a 250-mL flask, gently mixed and then diluted. 15 mL of lymphocyte separation solution Ficoll-Paque PREMIUM was added to a 50-mL PBMC separation tube SepMateTM-50 before 30 mL of diluted blood was added. The mixture was centrifuged at 1200 g at room temperature for 10 min. The supernatant was collected, and then centrifuged at 300 g for 8 min. The cells were resuspended in RMPI 1640 culture medium containing 10% FBS, counted and adjusted to $3.33 \times 10^6$ cells/mL. 150 μL of the suspension was added to the cell culture plate containing the compound, and incubated for 24 h at 37° C./5.0% $CO_2$. The plate was centrifuged at 1200 rpm for 10 min at room temperature and 150 μL of supernatant was taken from each well.

The reagents of the Human IL-12 detection kit was equilibrated to room temperature. The maximum concentration of the standard substance was 2000 pg/mL according to the kit instruction, which was serially two-fold diluted to the $8^{th}$ concentration. The test samples were 20-fold diluted, added to the pre-coated plate at 100 μL/well, and incubated at 37° C. for 90 min. The plate was washed before the antibiotic antibody was added at 100 μL/well, and incubated at 37° C. for 60 min. The plate was washed before the conjugated HRP was added at 100 μL/well, incubated at 37° C. for 30 min and washed; TMB was added and the plate was again incubated at room temperature for 5 min. Finally, a terminating solution was added to terminate the reaction, and the plate was detected for the absorbance at 450 nm using a microplate reader.

The reagents of the Human IFNγ detection kit was equilibrated to room temperature. The standard substance and the detection antibody were prepared in the dark according to the kit instruction. 16 μL of supernatant obtained by centrifugation was added into each well before 4 μL of mixed detection antibody was added. The plate was well mixed by shaking, incubated overnight in the dark at room temperature, and detected using PHERAStar with an htrf program.

The concentration of a compound that can stimulate a 3-fold higher SD than the mean SD of the untreated group is defined as the MEC (minimum effective concentration) of the compound.

The ability of the compound disclosed herein to stimulate IL-12 and IFNγ secretion in PBMCs was determined by the above test and the MEC values obtained are shown in Table 1-5.

TABLE 1-5

| MEC of the compound disclosed herein for stimulating IL-12 and IFNγ secretion in PBMCs | | |
| --- | --- | --- |
| Example | IL-12 MEC (nM) | IFNγ MEC (nM) |
| 1 | 41 | — |

Conclusion: from the data for the activity for stimulating IL-12 and IFNγ secretion in PBMCs, the compound disclosed herein has the advantage of a lower effective concentration.

Test Example 6

1. Objective
The blocking effect of the compound disclosed herein on hERG potassium current was tested on a stable cell line transfected with hERG potassium channel using automatic patch clamping.
2. Methodology
2.1 Materials and instruments
2.1.1 Materials:

| Reagent | Supplier | Catalog No. |
| --- | --- | --- |
| FBS | GIBCO | 10099 |
| Sodium pyruvate solution | Sigma | S8636-100ML |
| MEM non-essential amino acid solution (100×) | Sigma | M7145-100ML |

-continued

| Reagent | Supplier | Catalog No. |
| --- | --- | --- |
| G418 sulfate | Enzo | ALX-380-013-G005 |
| MEM | Hyclone | SH30024.01B |
| hERG cDNA | Origene | — |

2.1.2 Instruments:

| Instrument | Supplier | Model No. |
| --- | --- | --- |
| Patchliner 4-channel | Nanion | 2-03-03100-002 |
| Patchliner cleaning station | Nanion | 2-02-03201-005 |
| Patchliner cell bank | Nanion | 2-02-03105-000 |
| Elektrodenchloridierer Patchliner | Nanion | 3-02-03533-000 |
| HEAK EPC 10 patch clamp amplifier | Nanion | 1-01-10012-000 |
| Osmometer | Gonoter | Gonoter 030 |
| pH meter | Mettle Toledo | FE20 |

2.2 Automatic Patch Clamping Procedures

HEK293-hERG stable cell line was subcultured at a density of 1:4 in MEM/EBSS culture medium (10% FBS, 400 μg/mL G418, 1% MEM non-essential amino acid solution (100×), 1% sodium pyruvate solution). The automatic patch clamping was performed within 48-72 hours of culture. On the day of experiment, the cells were digested with 0.25% trypsin, collected by centrifugation and resuspended in an extracellular fluid (140 mM NaCl, 4 mM KCl, 1 mM $MgCl_2$, 2 mM $CaCl_2$, 5 mMD glucose monohydrate, 10 mM Hepes, pH 7.4, 298 mOsmol) to prepare a cell suspension. The cell suspension was placed on the cell bank of the Patchliner instrument that transferred the cells to the chip (NPC-16) using a negative pressure controller. The negative pressure held the individual cells in the wells of the chip. When the whole cell mode was formed, the instrument generated hERG current according to the setting of hERG current voltage program, and automatically perfused the compound solutions from low concentration to high concentration. The currents at various concentrations of the compound and in the blank control were analyzed by data analysis software provided by HEAK Patchmaster, HEAK EPC10 patch clamp amplifier (Nanion) and Pathlinersoftware and Pathcontrol HTsoftware.

2.3 Results

The blocking effect of the compound disclosed herein on hERG potassium current can be determined by the above test, and the $IC_{50}$ values obtained are shown in Table 1-6.

TABLE 1-6

| $IC_{50}$ for blocking effect of the compound disclosed herein on hERG potassium current | |
| --- | --- |
| Example | $IC_{50}$ (μM) |
| 1 | 26 |

Conclusion: the compound disclosed herein has a weak inhibitory effect on hERG and can reduce side effects caused by the hERG pathway.

The invention claimed is:

1. A crystalline form of a compound of formula (I):

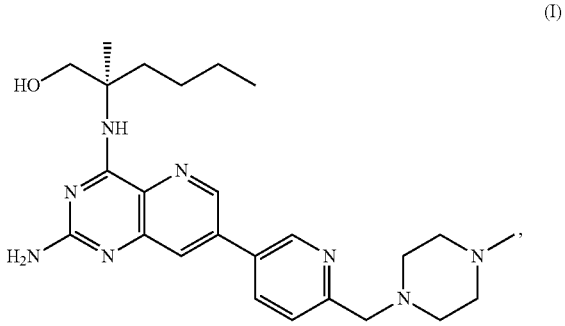 [SMILES: CCCC[C@](C)(CO)Nc1nc(N)nc2cc(-c3ccc(CN4CCN(C)CC4)nc3)cnc12]

selected from the group consisting of crystalline form A and crystalline form B, wherein:
the crystalline form A has an X-ray powder diffraction pattern with characteristic peaks at 2θ angles of 8.610, 9.740, 13.903, 15.313, 16.354, 17.675, 17.879, 19.184, 19.905, 20.901, 21.365, 22.319 and 23.057; and
the crystalline form B has an X-ray powder diffraction pattern with characteristic peaks at 2θ angles of 4.60, 8.77, 9.90, 13.86, 15.45, 16.44, 17.74, 18.03, 19.31, 19.91, 21.07, 21.52, 22.48 and 23.22.

2. The crystalline form according to claim 1, wherein the crystalline form is crystalline form A.

3. The crystalline form according to claim 2, wherein the crystalline form A has an X-ray powder diffraction pattern with characteristic peaks at 2θ angles of 8.610, 9.740, 10.949, 13.314, 13.903, 15.313, 16.060, 16.354, 16.794, 17.675, 17.879, 19.184, 19.905, 20.901, 21.365, 22.319, 23.057, 23.748, 24.430, 25.428, 26.576, 27.270, 27.863, 28.957, 29.842 and 31.506.

Figure 2:
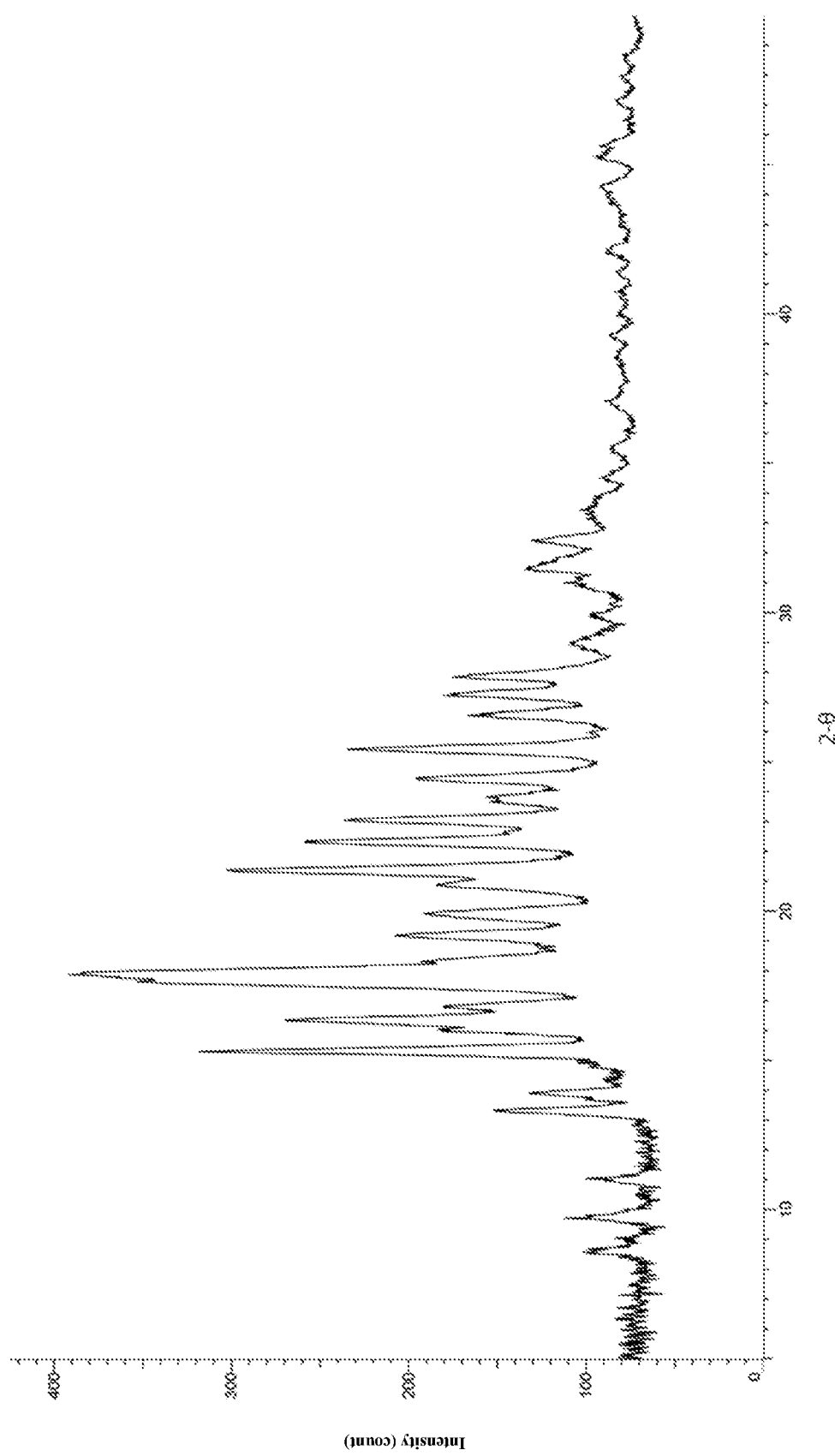
FIG. 2 is an XRPD pattern for the crystalline form A of the compound of formula (I).
Figure 3:
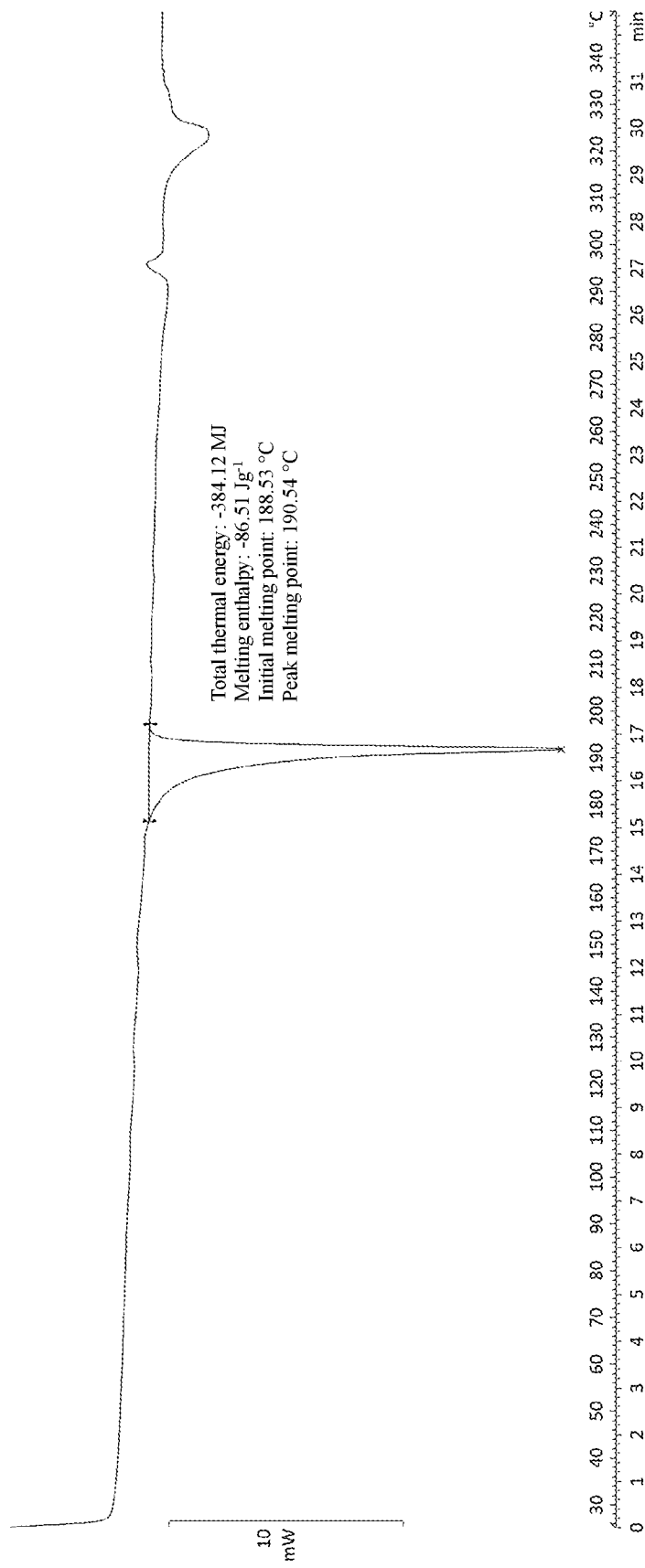
FIG. 3 is a DSC pattern for the crystalline form A of the compound of formula (I).

4. The crystalline form A of the compound of formula (I) according to claim 2, having an X-ray powder diffraction pattern as shown in FIG. 2.

5. The crystalline form according to claim 1, wherein the crystalline form is crystalline form B.

6. The crystalline form according to claim 5, wherein the crystalline form B has an X-ray powder diffraction pattern with characteristic peaks at 2θ angles of 4.60, 8.77, 9.20, 9.90, 11.17, 13.86, 14.51, 15.45, 16.44, 17.74, 18.03, 18.19, 18.51, 19.31, 19.91, 20.07, 21.07, 21.52, 22.48, 23.22, 24.00, 24.61, 25.64, 26.78, 27.43, 28.04, 29.31, 31.21, 32.09, 32.57, 33.23 and 34.01.

Figure 4:
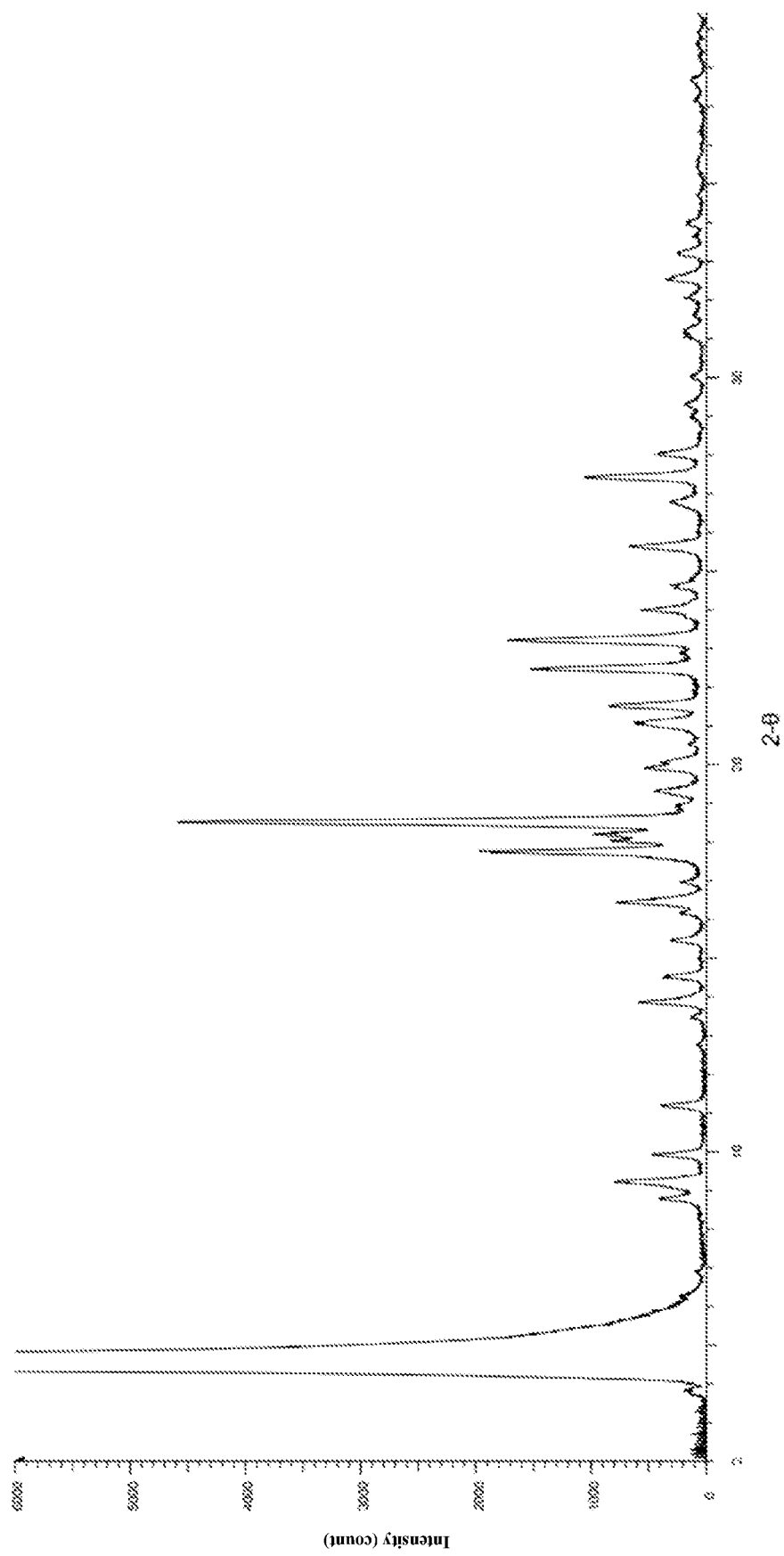
FIG. 4 is an XRPD pattern for the crystalline form B of the compound of formula (I).
Figure 5:
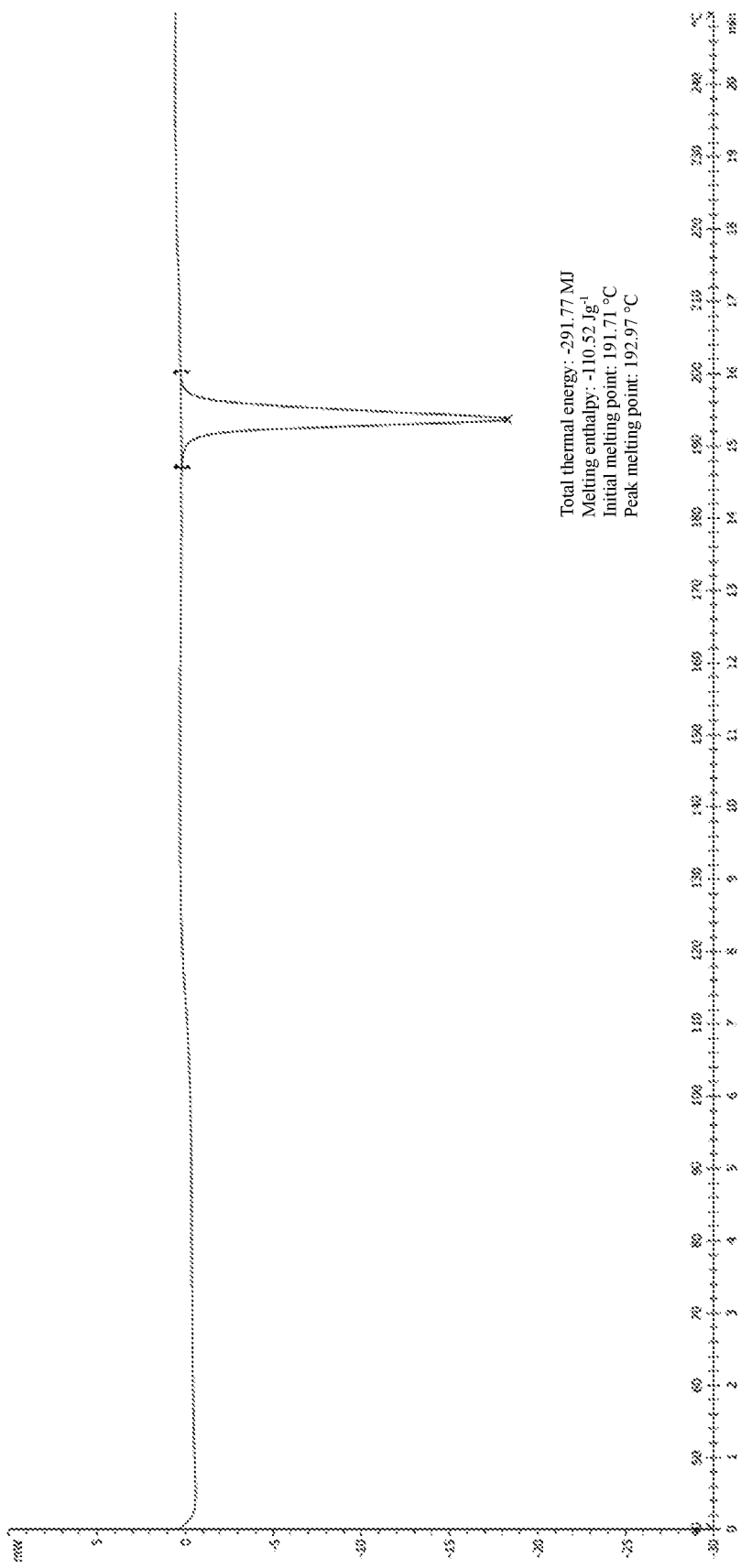
FIG. 5 is a DSC pattern for the crystalline form B of the compound of formula (I).
Figure 6:
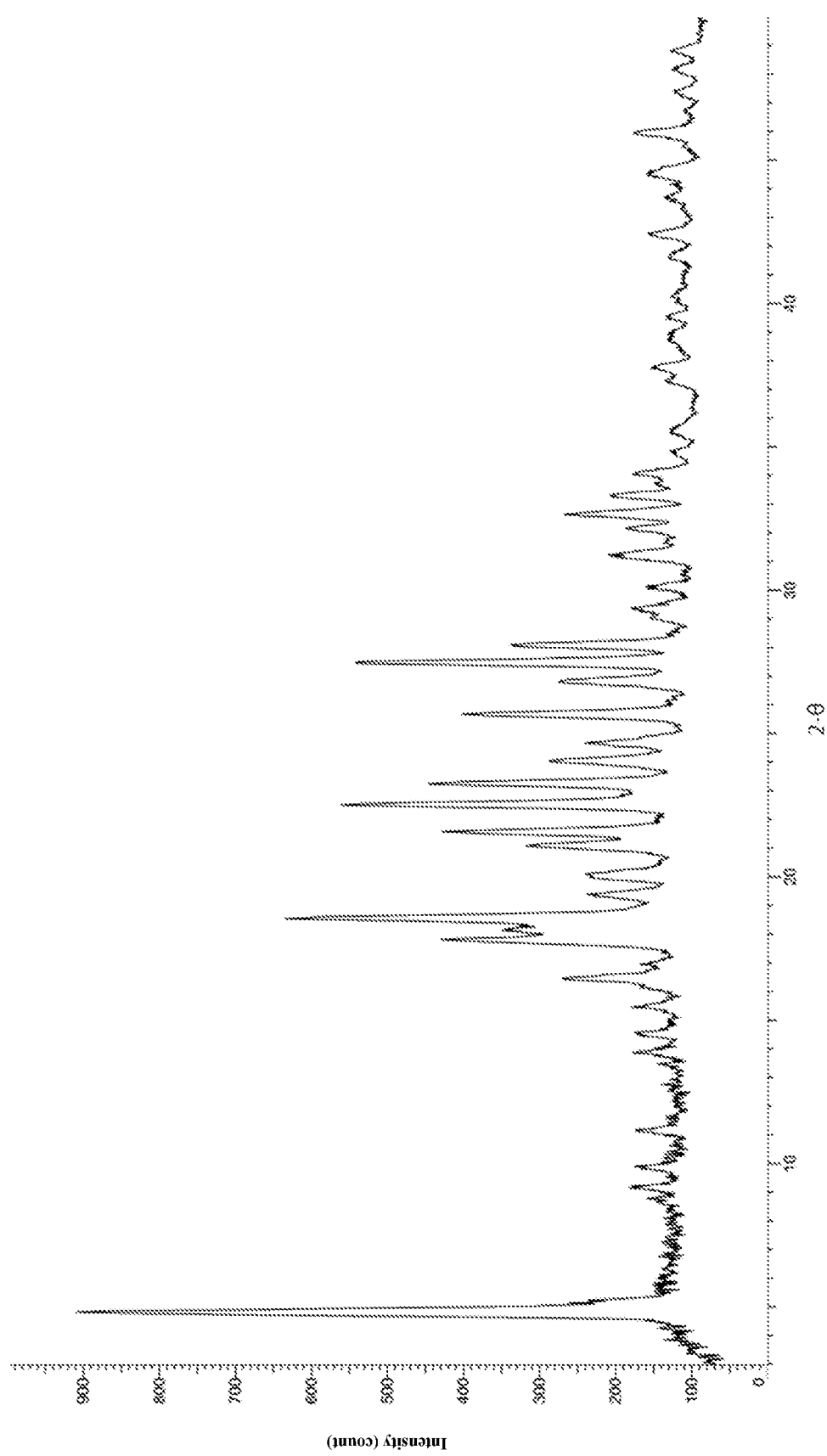
FIG. 6 is an XRPD pattern for a mixture of the crystalline form A and the crystalline form B of the compound of formula (I).

7. The crystalline form B of the compound of formula (I) according to claim 5, having an X-ray powder diffraction pattern as shown in FIG. 4.

8. The crystalline form of the compound of formula (I) according to claim 1, wherein the angle 2θ has a margin of error of ±0.2.

9. A method for preparing the crystalline form A of the compound of formula (I) according to claim 2, the method comprising: mixing the compound of formula (I) with a proper amount of a solvent, and evaporating for crystallization, wherein the solvent is selected from the group consisting of one or more of methanol, n-heptane, cyclohexane, n-hexane, petroleum ether and n-propanol; or mixing the compound of formula (I) with a proper amount of a solvent, heating for dissolution, and cooling for crystallization, wherein the solvent is ethyl acetate.

10. A method for preparing the crystalline form B of the compound of formula (I) according to claim 5, the method comprising: mixing the compound of formula (I) with a proper amount of a solvent, and evaporating for crystallization, wherein the solvent is selected from the group consisting of one or more of water, isopropanol, ethyl acetate, acetonitrile, acetophenone, dichloromethane, N,N-dimethylformamide and 1,2-dichloroethane; or mixing the compound of formula (I) with a proper amount of a solvent, heating for dissolution, and cooling for crystallization, wherein the solvent is selected from the group consisting of isopropanol and dimethyl sulfoxide.

11. A pharmaceutical composition comprising the crystalline form according to claim 1, and one or more pharmaceutically acceptable carriers or excipients.

12. A pharmaceutical composition prepared by mixing the crystalline form according to claim 1 with one or more pharmaceutically acceptable carriers or excipients.

13. A method for treating a disease with TLR8 agonist in a subject in need thereof comprising administering to the subject an effective amount of the pharmaceutical composition according to claim 11.

14. A method for treating an infection caused by a virus in a subject in need thereof comprising administering to the subject an effective amount of the pharmaceutical composition according to claim 11, wherein the virus is one or more of hepatitis B virus, hepatitis C virus, influenza virus, herpes virus and human immunodeficiency virus.

15. A method for modulating immune system in a subject in need thereof comprising administering to the subject an effective amount of the pharmaceutical composition according to claim 11.

16. A method for treating a tumor in a subject in need thereof comprising administering to the subject an effective amount of the pharmaceutical composition according to claim 11.

17. A method for preparing the pharmaceutical composition according to claim 12, comprising: mixing the crystalline form A and/or the crystalline form B of the compound of formula (I) with one or more pharmaceutically acceptable carriers or excipients.

* * * * *